(12) United States Patent
Wakui

(10) Patent No.: US 11,009,689 B2
(45) Date of Patent: May 18, 2021

(54) OBSERVATION DEVICE, OBSERVATION METHOD, AND OBSERVATION DEVICE CONTROL PROGRAM

(71) Applicant: FUJIFILM Corporation, Tokyo (JP)

(72) Inventor: Takashi Wakui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 260 days.

(21) Appl. No.: 16/177,577

(22) Filed: Nov. 1, 2018

(65) Prior Publication Data
US 2019/0072749 A1 Mar. 7, 2019

Related U.S. Application Data

(63) Continuation of application No. PCT/JP2017/008563, filed on Mar. 3, 2017.

(30) Foreign Application Priority Data

May 17, 2016 (JP) .............................. JP2016-098541

(51) Int. Cl.
  *G02B 21/00* (2006.01)
  *G02B 7/28* (2021.01)
  *G02B 21/24* (2006.01)
  *C12N 5/07* (2010.01)
  (Continued)

(52) U.S. Cl.
  CPC ........... *G02B 21/0036* (2013.01); *C12N 5/06* (2013.01); *G02B 7/28* (2013.01); *G02B 21/002* (2013.01);
  (Continued)

(58) Field of Classification Search
  CPC .... G02B 21/0036; G02B 7/28; G02B 21/241; G02B 21/002; G02B 21/008; G02B 21/02; G02B 21/26; G02B 21/00; C12N 5/06
  See application file for complete search history.

(56) References Cited

U.S. PATENT DOCUMENTS

2003/0184855 A1* 10/2003 Yasuda ................ G02B 21/241
                                                                359/383
2005/0089208 A1    4/2005 Dong et al.
(Continued)

FOREIGN PATENT DOCUMENTS

CN      103852878 A    6/2014
JP      10-307252 A    11/1998
(Continued)

OTHER PUBLICATIONS

Communication dated Nov. 26, 2019 from Japanese Patent Office in counterpart JP Application No. 2016-098541.
(Continued)

*Primary Examiner* — Robert E. Tallman
(74) *Attorney, Agent, or Firm* — Sughrue Mion, PLLC

(57) ABSTRACT

An observation device includes a stage, an imaging optical system that includes an objective lens, a detection section that includes displacement sensors that detect a vertical position of a cultivation container, an imaging optical system controller that controls the imaging optical system driving section to move the objective lens in an optical axis direction on the basis of the vertical position of the cultivation container, and a horizontal driving section that moves the stage in a main scanning direction and a sub-scanning direction and reciprocates the stage in the main scanning direction, in which the detection section detects the vertical position of the cultivation container at a forward position in a movement direction of the observation region with reference to the position of the observation region of the imaging optical system with respect to the cultivation container.

25 Claims, 6 Drawing Sheets

(51) Int. Cl.
  *G02B 21/02* (2006.01)
  *G02B 21/26* (2006.01)
(52) U.S. Cl.
  CPC .......... *G02B 21/008* (2013.01); *G02B 21/02* (2013.01); *G02B 21/241* (2013.01); *G02B 21/26* (2013.01)

(56) References Cited

U.S. PATENT DOCUMENTS

| 2015/0309297 A1 | 10/2015 | Westphal et al. | |
|---|---|---|---|
| 2016/0041380 A1* | 2/2016 | Kuhn | H04N 5/232121 348/79 |

FOREIGN PATENT DOCUMENTS

| JP | 2003-295065 A | 10/2003 |
| JP | 2008-083601 A | 4/2008 |
| JP | 2011-002715 A | 1/2011 |
| JP | 2011-81211 A | 4/2011 |
| WO | 2013/165576 A1 | 11/2013 |

OTHER PUBLICATIONS

Communication dated May 21, 2019 by the Japanese Patent Office in counterpart application No. 2016-098541.
Communication dated May 24, 2019 by European Patent Office in counterpart application No. 17798974.6.
Communication dated Jul. 25, 2019 by Korean Patent Office in counterpart application No. 10-2018-7031959.
International Search Report dated May 30, 2017, issued by the International Searching Authority in application No. PCT/JP2017/008563.
International Preliminary Report on Patentability with translation of Written Opinion dated Nov. 20, 2018, issued by the International Searching Authority in application No. PCT/JP2017/008563.
Written Opinion dated May 30, 2017, issued by the International Searching Authority in application No. PCT/JP2017/008563.
Communication dated Jul. 27, 2020, from the European Patent Office in application No. 17798974.6.
Notice of Final Rejection dated Jan. 31, 2020 from Korean Intellectual Property Office in Application No. 10-2018-7031959.

* cited by examiner

MOVEMENT DIRECTION (GOING WAY)

MOVEMENT DIRECTION (RETURNING WAY)

MOVEMENT DIRECTION (GOING WAY)

MOVEMENT DIRECTION (RETURNING WAY)

OBSERVATION DEVICE, OBSERVATION METHOD, AND OBSERVATION DEVICE CONTROL PROGRAM

CROSS-REFERENCE TO RELATED APPLICATIONS

This application is a Continuation of PCT International Application No. PCT/JP 2017/008563 filed on Mar. 3, 2017, which claims priority under 35 U.S.C. § 119(a) to Japanese Patent Application No. 2016-098541 filed on May 17, 2016. Each of the above application(s) is hereby expressly incorporated by reference, in its entirety, into the present application.

BACKGROUND OF THE INVENTION

1. Field of the Invention

The present invention relates to an observation device, an observation method, and a non-transitory computer readable recording medium storing an observation device control program for observing an entire image of an observation target by relatively moving a stage on which a container in which the observation target is contained and an imaging optical system that forms an image of the observation target.

2. Description of the Related Art

In the related art, a method for capturing an image of a multipotential stem cell such as an embryonic stem (ES) cell or an induced pluripotent stem (iPS) cell, a differentiated and induced cell, or the like using a microscope or the like, and capturing a feature of the image to decide a differentiation state of the cell, or the like has been proposed.

The multipotential stem cell such as an ES cell or an iPS cell is able to be differentiated into cells of various tissues, and may be applied to regenerative medicine, development of medicines, explanation of diseases, or the like.

On the other hand, in a case where a cell is imaged using a microscope as described above, in order to acquire a high-magnification wide view image, for example, a so-called tiling imaging technique for scanning the inside of a range of a cultivation container such as a well plate in accordance with an observation region of an imaging optical system and capturing an image for each observation region, and then, combining the images for the respective observation regions has been proposed.

SUMMARY OF THE INVENTION

Here, in a case where an image for each observation region as described above is captured, there are many cases where a focal position of the imaging optical system is formed on a bottom surface of the cultivation container. However, the thickness of a bottom portion of the cultivation container has a millimeter-order fabrication tolerance, and thus, in a case where high-magnification imaging is performed, it is necessary to adjust the focal position for each observation region. On the other hand, it is desirable to reduce a cell imaging time, and to provide a device capable of performing high-speed imaging.

However, in a related-art auto-focus control method, about 2 seconds are necessary for each observation region, and for example, in a case where the number of observation regions is 300, it takes 100 minutes only for the time necessary for the auto-focus control, which makes it impossible to perform high-speed imaging.

JP2011-81211A discloses a method for precedently measuring, at a time point when an image of a certain observation region is captured, a focal position at a region contiguous to the observation region so as to shorten an imaging time and performing a focus control using the focal position that is previously measured to perform capturing of images.

However, according to JP2011-81211A, in a case where the focal position is measured, similar to the case of the related-art auto-focus control, since an image of the region contiguous to the observation region is captured and the focal position is measured on the basis of contrast of the image, it takes time for an operation process. Accordingly, in a case where a stage is moved at high speed, there is a possibility that an operation process and an auto-focus control based on the operation process and a result of the operation process at a time point when an observation region reaches a measurement position do not match each other.

Further, JP2011-81211A merely discloses a method for scanning an observation region in only one direction, and in the scanning in only one direction, a scanning time becomes extremely long.

In consideration of the above-mentioned problems, an object of the present invention is to provide an observation device, an observation method, and a non-transitory computer readable recording medium storing an observation control program capable of performing an auto-focus control for each observation region at high speed and shortening a scanning time of observation regions in an entire range.

According to an aspect of the invention, there is provided an observation device comprising: a stage on which a container in which an observation target is contained is provided; an imaging optical system that includes an objective lens for forming an image of the observation target in the container; an imaging optical system driving section that moves the objective lens in an optical axis direction; a detection section that includes at least one displacement sensor that detects a vertical position of the container provided on the stage; an imaging optical system controller that controls the imaging optical system driving section on the basis of the vertical position of the container detected by the detection section; a horizontal driving section that moves at least one of the stage or the imaging optical system in a main scanning direction in a horizontal plane and a sub-scanning direction orthogonal to the main scanning direction, and reciprocates the at least one of the stage or the imaging optical system in the main scanning direction; and a scanning controller that controls the horizontal driving section, in which the detection section detects the vertical position of the container at a forward position in a movement direction of an observation region with reference to the position of the observation region of the imaging optical system with respect to the container, and changes a position of the displacement sensor in the main scanning direction or the displacement sensor to be used in accordance with a change of the movement direction in the main scanning direction.

Further, in the observation device of the invention, the detection section may include at least two displacement sensors that are provided in parallel in the main scanning direction with the objective lens being interposed therebetween, and may change the displacement sensor to be used in accordance with the change of the movement direction in the main scanning direction.

Further, in the observation device of the invention, the detection section may include a displacement sensor moving mechanism capable of moving the displacement sensor in the main scanning direction between one side and the other side with the objective lens being interposed therebetween, and may move the position of the displacement sensor from the one side to the other side in accordance with the change of the movement direction in the main scanning direction.

Further, in the observation device of the invention, the displacement sensor moving mechanism may include a guide mechanism that guides the displacement sensor from the one side to the other side.

Further, in the observation device of the invention, the imaging optical system controller may control the imaging optical system driving section to move the objective lens in the optical axis direction at a time point when a predetermined time elapses after the vertical position of the container is detected by the detection section.

Further, in the observation device of the invention, the imaging optical system controller may control the imaging optical system driving section to move the objective lens in the optical axis direction at a time point when the observation region of the imaging optical system reaches the detected position or immediately before the observation region of the imaging optical system reaches the detected position after the vertical position of the container is detected by the detection section.

Further, in the observation device of the invention, the imaging optical system controller may change, in a case where a moving velocity of at least one of the stage or the imaging optical system is changed by the scanning controller, the predetermined time in accordance with the moving velocities before and after the change.

Further, in the observation device of the invention, it is preferable that the acceleration-deceleration regions for movement of at least one of the stage or the imaging optical system in the main scanning direction are set on both sides of the main scanning direction in the range of the container, and a width of the acceleration-deceleration region in the main scanning direction and an interval in the main scanning direction between the imaging optical system and the displacement sensor are equal to each other.

Further, the observation device may further comprise a vertically moving mechanism that integrally moves the imaging optical system, the imaging optical system driving section, and the displacement sensor in a vertical direction.

Further, in the observation device of the invention, the imaging optical system driving section may include a piezoelectric element, and may move the objective lens in the optical axis direction using the piezoelectric element.

Further, in the observation device of the invention, the displacement sensor may use a laser displacement sensor.

According to another aspect of the invention, there is provided an observation method for moving at least one of a stage on which a container in which an observation target is contained is provided or an imaging optical system that includes an objective lens for forming an image of the observation target in the container in a main scanning direction and a sub-scanning direction orthogonal to the main scanning direction and reciprocating the at least one of the stage or the imaging optical system in the main scanning direction, the method comprising: detecting a vertical position of the container at a forward position in a movement direction of an observation region with reference to the position of the observation region of the imaging optical system with respect to the container using at least one displacement sensor; moving the objective lens in an optical axis direction on the basis of the detected vertical position of the container; and changing a position of the displacement sensor in the main scanning direction or the displacement sensor to be used in accordance with a change of the movement direction in the main scanning direction.

According to still another aspect of the invention, there is provided a non-transitory computer readable recording medium storing an observation device control program that causes a computer to execute a procedure for moving at least one of a stage on which a container in which an observation target is contained is provided or an imaging optical system that includes an objective lens for forming an image of the observation target in the container in a main scanning direction and a sub-scanning direction orthogonal to the main scanning direction and reciprocating the at least one of the stage or the imaging optical system in the main scanning direction, the program comprising: a step of detecting a vertical position of the container at a forward position in a movement direction of an observation region with reference to the position of the observation region of the imaging optical system with respect to the container using at least one displacement sensor; a step of moving the objective lens in an optical axis direction on the basis of the detected vertical position of the container; and a step of changing a position of the displacement sensor in the main scanning direction or the displacement sensor to be used in accordance with a change of the movement direction in the main scanning direction.

According to the observation device, the observation method, and the non-transitory computer readable recording medium storing an observation device control program, at least one of a stage on which a container is provided or an imaging optical system that forms an image of an observation target in the container is moved in a main scanning direction and a sub-scanning direction, and the at least one of the stage or the imaging optical system is reciprocated with respect to the main scanning direction. In this way, by reciprocating the stage or the imaging optical system in the main scanning direction to scan the observation region of the imaging optical system, it is possible to shorten a scanning time of the observation region, compared with a case where the stage is moved in only one direction to scan the observation region as disclosed in JP2011-81211A.

Further, since an auto-focus control is performed by detecting a vertical position of a container at a forward position in a movement direction of an observation region with reference to the position of the observation region of the imaging optical system with respect to the container using at least one displacement sensor, and moving an objective lens in an optical axis direction on the basis of the vertical position of the detected container, it is possible to perform an auto-focus control at high speed, compared with a case where an auto-focus control is performed on the basis of a contrast of an image captured as disclosed in JP2011-81211A.

In addition, according to the invention, since a position of the displacement sensor in the main scanning direction or the displacement sensor to be used in accordance with a change of the movement direction in the main scanning direction is changed, even in a case where the observation region is reciprocated, it is possible to detect the position of the container prior to capturing of an image.

DESCRIPTION OF THE PREFERRED EMBODIMENTS

Figure 1:
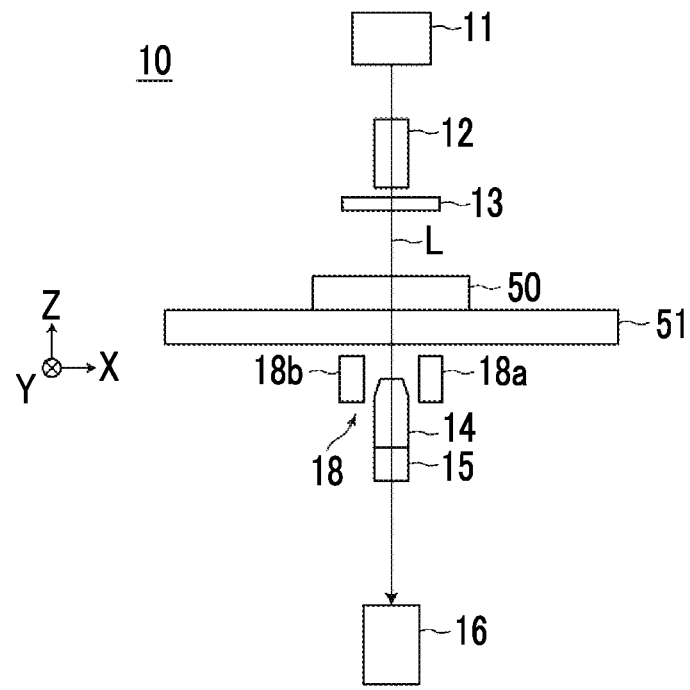
FIG. 1 is a diagram showing a schematic configuration of a microscope observation system that uses an observation device according to a first embodiment of the present invention.

Hereinafter, a microscope observation system that uses an observation device, an observation method, and an observation device control program according to a first embodiment of the invention will be described with reference to the accompanying drawings. FIG. 1 is a block diagram showing a schematic configuration of a microscope device 10 in a microscope observation system of the embodiment.

The microscope device 10 captures a phase difference image of a cultivated cell that is an observation target. Specifically, the microscope device 10 includes a white light source 11 that emits white light, a condenser lens 12, a slit plate 13, an imaging optical system 14, an imaging optical system driving section 15, an imaging element 16, and a detection section 18, as shown in FIG. 1.

The slit plate 13 has a configuration in which a ring-shaped slit through which white light passes is formed in a light-shielding plate that shields white light emitted from the white light source 11. As the white light passes through the slit, ring-shaped illumination light L is formed.

Figure 2:
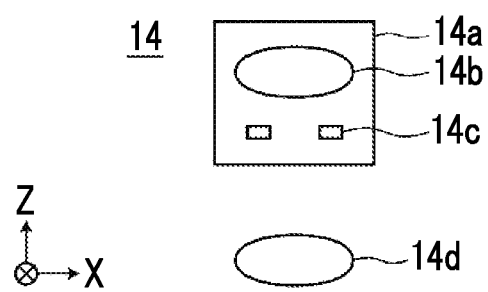
FIG. 2 is a schematic diagram showing a configuration of an imaging optical system.

FIG. 2 is a diagram showing a detailed configuration of the imaging optical system 14. The imaging optical system 14 includes a phase difference lens 14a and an imaging lens 14d, as shown in FIG. 2. The phase difference lens 14a includes an objective lens 14b and a phase plate 14c. The phase plate 14c has a configuration in which a phase ring is formed in a transparent plate that is transparent with respect to a wavelength of the illumination light L. The size of the slit of the above-described slit plate 13 is in a conjugate relation with the phase ring of the phase plate 14c.

The phase ring has a configuration in which a phase membrane that shifts a phase of incident light by ¼ of a wavelength and a light-reducing filter that reduces incident light are formed in a ring shape. The phase of direct light incident onto the phase ring shifts by ¼ of a wavelength after passing through the phase ring, and its brightness is weakened. On the other hand, most of diffracted light diffracted by an observation target passes through the transparent plate of the phase plate 14c, and its phase and brightness are not changed.

The phase difference lens 14a having the objective lens 14b is moved in an optical axis direction of the objective lens 14b by the imaging optical system driving section 15 shown in FIG. 1. In this embodiment, the objective lens 14b, the optical axis direction, and a Z direction (vertical direction) are the same direction. An auto-focus control is performed as the phase difference lens 14a is moved in the Z direction, and contrast of a phase difference image captured by the imaging element 16 is adjusted.

Further, a configuration in which a magnification of the phase difference lens 14a is changeable may be used. Specifically, a configuration in which the phase difference lenses 14a or the imaging optical systems 14 having different magnifications are interchangeable may be used. The interchange between the phase difference lens 14a and the imaging optical systems 14 may be automatically performed, or may be manually performed by a user.

The imaging optical system driving section 15 includes an actuator such as a piezoelectric element, for example, and performs driving on the basis of a control signal output from an imaging optical system controller 21 (which will be described later). The imaging optical system driving section 15 is configured to pass a phase difference image passed through the phase difference lens 14a as it is. Further, the configuration of the imaging optical system driving section 15 is not limited to the piezoelectric element. A configuration in which the phase difference lens 14a is movable in the Z direction may be used, and known different configurations may be used.

The imaging lens 14d receives a phase difference image passed through the phase difference lens 14a and the imaging optical system driving section 15 and incident thereto, and causes an image based on the phase difference image to be formed on the imaging element 16.

The imaging element 16 captures an image on the basis of the phase difference image formed by the imaging lens 14d. As the imaging element 16, a charge-coupled device (CCD) image sensor, a complementary metal-oxide semiconductor (CMOS) image sensor, or the like may be used. As the imaging element, an imaging element in which color filters of red, green, and blue (R, G, and B) are provided may be used, or a monochromic imaging element may be used.

The detection section 18 detects a Z-directional (vertical) position of a cultivation container 50 provided on a stage 51. Specifically, the detection section 18 includes a first displacement sensor 18a and a second displacement sensor 18b. The first displacement sensor 18a and the second displacement sensor 18b are provided in parallel in the X direction shown in FIG. 1 with the phase difference lens 14a being interposed therebetween. The first displacement sensor 18a and the second displacement sensor 18b in this embodiment are laser displacement meters, which irradiate the cultivation container 50 with laser light and detect its reflection light to detect a Z-directional position of a bottom surface of the cultivation container 50. The bottom surface of the cultivation container 50 refers to a boundary surface between a bottom portion of the cultivation container 50 and cells that are observation targets, that is, a surface on which the observation targets are placed.

Information on the Z-directional position of the cultivation container 50 detected by the detection section 18 is output to the imaging optical system controller 21, and the imaging optical system controller 21 controls the imaging optical system driving section 15 on the basis of the input position information to perform the auto-focus control. The detection of the position of the cultivation container 50 based on the first displacement sensor 18a and the second displacement sensor 18b and the auto-focus control in the imaging optical system controller 21 will be described later.

Between the slit plate 13, and the phase difference lens 14a and the detection section 18, the stage 51 is provided. On the stage 51, the cultivation container 50 in which cells that are observation targets are contained is provided.

As the cultivation container 50, a schale, a dish, a well plate, or the like may be used. Further, as cells contained in the cultivation container 50, multipotential stem cells such as induced pluripotent stem (iPS) cells and embryonic stem (ES) cells, cells of nerves, the skin, the myocardium and the liver, which are differentiated and induced from a stem cell, cells of the skin, the retina, the myocardium, blood corpuscles, nerves, and organs extracted from a human body, and the like, may be used.

The stage 51 is moved in the X direction and a Y direction that are orthogonal to each other by the horizontal driving direction 17 (see FIG. 4) (which will be described later). The X direction and the Y direction are directions orthogonal to the Z direction, and are directions that are orthogonal to each other in a horizontal plane. In this embodiment, the X direction is referred to as a main scanning direction, and the Y direction is referred to as a sub-scanning direction.

Figure 3:
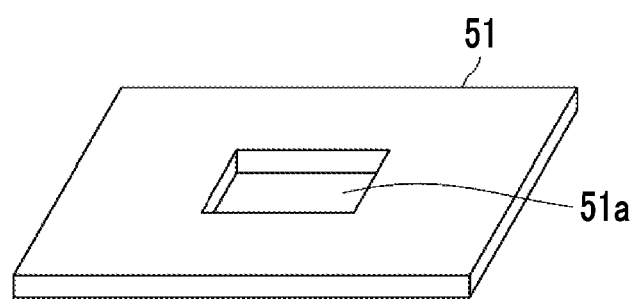
FIG. 3 is a perspective view showing a configuration of a stage.

FIG. 3 is a diagram showing an example of the stage 51. At the center of the stage 51, a rectangular opening 51a is formed. The cultivation container 50 is provided on a member that is formed with the opening 51a, and a cell phase difference image of a cell in the cultivation container 50 passes through the opening 51a.

Figure 4:
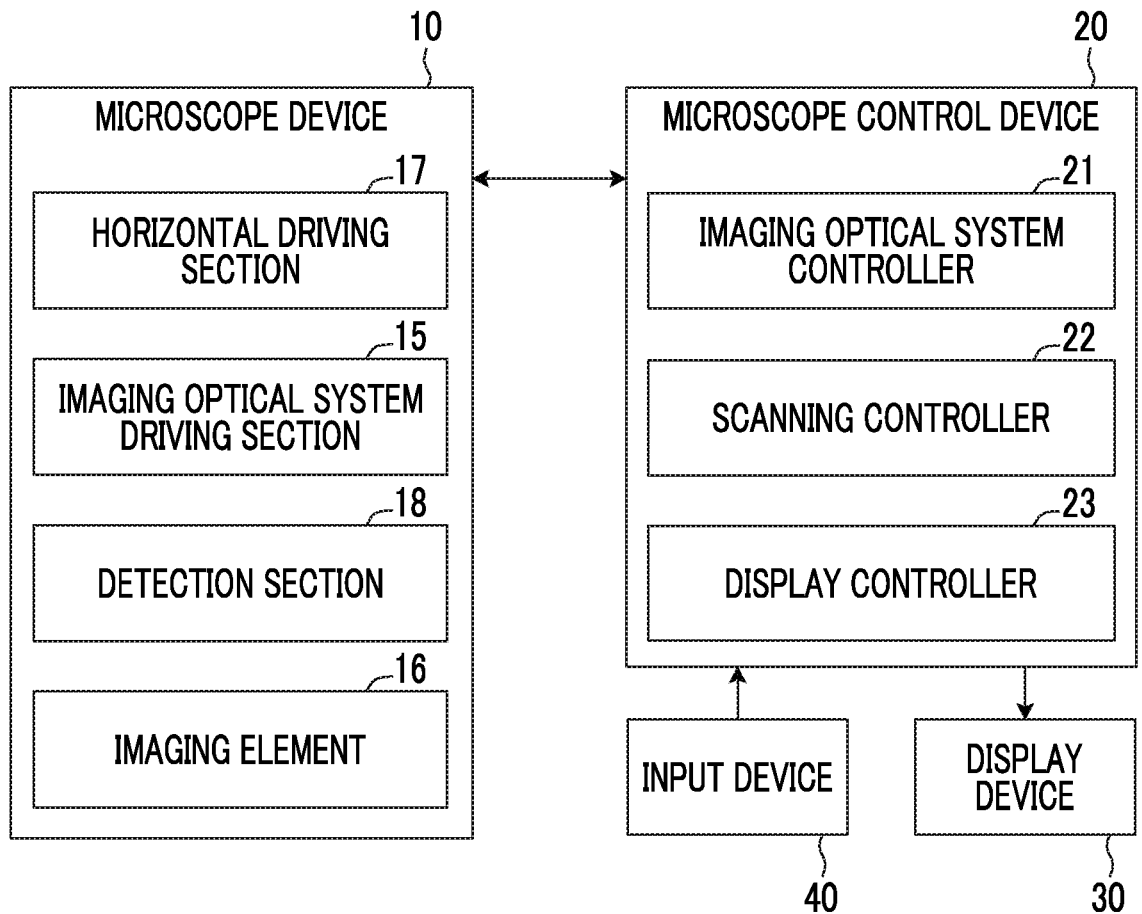
FIG. 4 is a block diagram showing a schematic configuration of the microscope observation system that uses the observation device according to the first embodiment of the invention.

Then, a configuration of the microscope control device 20 that controls the microscope device 10 will be described. FIG. 4 is a block diagram showing a configuration of a microscope observation system according to this embodiment. With respect to the microscope device 10, a block diagram of a partial configuration controlled by respective sections of the microscope control device 20 is shown.

The microscope control device 20 generally controls the microscope device 10, and particularly, includes an imaging optical system controller 21, a scanning controller 22, and a display controller 23.

The microscope control device 20 is configured of a computer including a central processing unit, a semiconductor memory, a hard disk, and the like. An embodiment of an observation device control program of the invention is installed in the hard disk. Further, as the observation device control program is executed by the central processing unit, the imaging optical system controller 21, the scanning controller 22, and the display controller 23 shown in FIG. 4 execute functions.

The imaging optical system controller 21 controls the imaging optical system driving section 15 on the basis of the Z-directional position information of the cultivation container 50 detected by the detection section 18 as described above. Further, the objective lens 14b of the imaging optical system 14 is moved in the optical axis direction by driving of the imaging optical system driving section 15, so that the auto-focus control is performed.

The scanning controller 22 controls driving of the horizontal driving section 17, so that the stage 51 is moved in the X direction and the Y direction. The horizontal driving section 17 is configured of an actuator having a piezoelectric element, or the like.

Hereinafter, the movement control of the stage 51 by the scanning controller 22 and the auto-focus control by the imaging optical system controller 21 will be described in detail.

Figure 5:
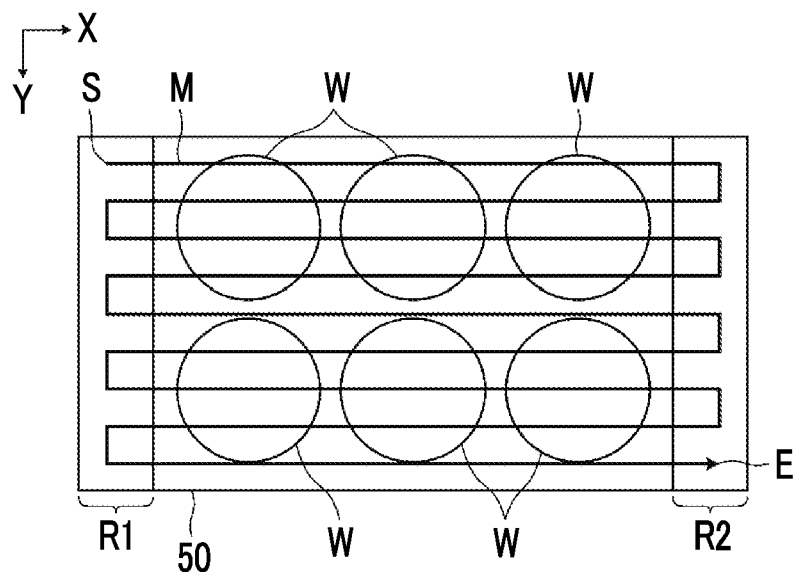
FIG. 5 is a diagram showing a scanning position of an observation region in a cultivation container.

In this embodiment, the stage 51 is moved in the X direction and the Y direction by the control of the main scanning controller 22, an observation region of the imaging optical system 14 is scanned in the cultivation container 50 in a two-dimensional form, and a phase difference image in each observation region is captured. FIG. 5 is a diagram showing a scanning position of an observation region in the cultivation container 50 using a solid line M. In this embodiment, a well plate having six wells W is used as the cultivation container 50.

As shown in FIG. 5, the observation region of the imaging optical system 14 is moved from a scanning start point S to a scanning end point E along the solid line M. That is, the observation region is scanned in a positive direction (a rightward direction in FIG. 5) of the X direction, is moved in the Y direction (a lower direction in FIG. 5), and then, is scanned in a reverse negative direction (in a left direction in FIG. 5). Then, the observation region is moved in the Y direction again, and then, is scanned in the positive direction again. In this way, by repeating the reciprocation in the X direction and the movement in the Y direction, the observation region is scanned in the cultivation container 50 in a two-dimensional form.

Figure 6:
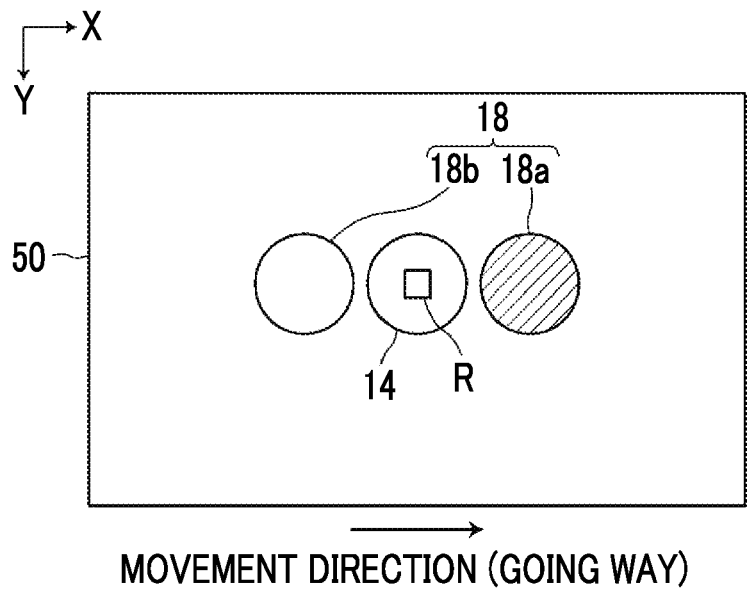
FIG. 6 is a diagram showing a positional relationship between an imaging optical system, a first displacement sensor and a second displacement sensor, and the cultivation container in a case where an observation region is disposed at a predetermined position in the cultivation container.
Figure 7:
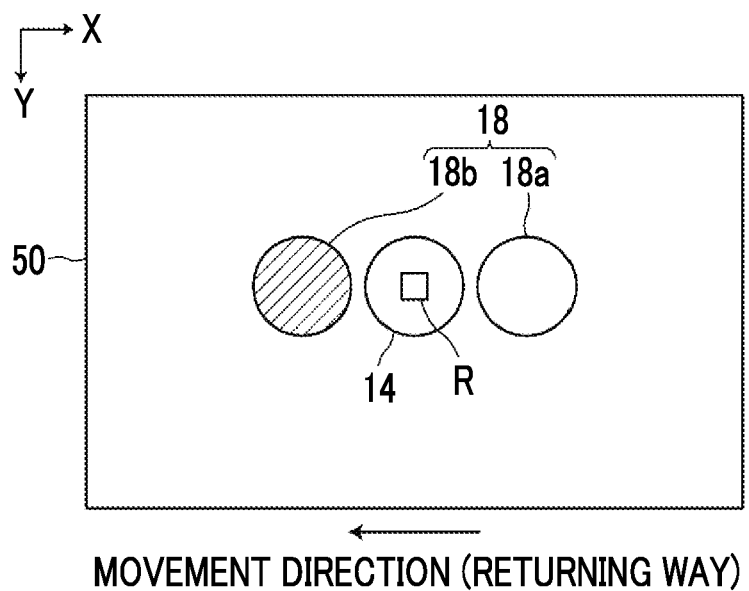
FIG. 7 is a diagram illustrating switching between the first displacement sensor and the second displacement sensor.

FIGS. 6 and 7 are diagrams showing a positional relationship between the imaging optical system 14, the first displacement sensor 18a and the second displacement sensor 18b, and the cultivation container 50 in a case where an observation region R is disposed at a predetermined position in the cultivation container 50.

In this embodiment, as shown in FIGS. 6 and 7, the first displacement sensor 18a and the second displacement sensor 18b are provided in parallel in the X direction with the imaging optical system 14 being interposed therebetween. Further, the observation region R of the imaging optical system 14 is scanned in the cultivation container 50 in a two-dimensional form as described above. Here, a Z-directional position of the cultivation container 50 is detected at a forward position of the observation region R in a movement direction with reference to the position of the observation region R of the imaging optical system 14 with respect to the cultivation container 50. Specifically, in a case where the observation region R is moved in an arrow direction shown in FIG. 6 (a rightward direction in FIG. 6), the Z-directional position of the cultivation container 50 is detected by the first displacement sensor 18a disposed on a forward side in the movement direction of the observation region R among the first displacement sensor 18a and the second displacement sensor 18b. Further, in a case where the observation region R is moved to the position of the first displacement sensor 18a from the position shown in FIG. 6, an auto-focus control is performed using information on the Z-directional position of the cultivation container 50 that is previously detected, and capturing of a phase difference image is performed.

On the other hand, in a case where the observation region R is moved in an arrow direction in FIG. 7 (a leftward direction in FIG. 7), the Z-directional position of the cultivation container 50 is detected by the second displacement sensor 18b disposed on a forward side in the movement direction of the observation region R among the first displacement sensor 18a and the second displacement sensor 18b. Further, in a case where the observation region R is moved to the position of the second displacement sensor 18b from the position shown in FIG. 7, an auto-focus control is performed using information on the Z-directional position of the cultivation container 50 that is previously detected, and capturing of a phase difference image is performed.

In this way, by performing switching between the detection of the cultivation container 50 using the first displacement sensor 18a and the detection of the cultivation container 50 using the second displacement sensor 18b in accordance with the movement direction of the observation regions R, it is possible to acquire information on the Z-directional position of the cultivation container 50 at the position of the observation region, prior to capturing of a phase difference image of the observation regions R.

Further, the imaging optical system controller 21 controls driving of the imaging optical system driving section 15 on the basis of the information on the Z-directional position of the cultivation container 50 that is previously detected as described above to perform an auto-focus control. Specifically, in the imaging optical system controller 21, a relationship between information on the Z-directional position of the cultivation container 50 and a movement amount of the imaging optical system 14 in the optical axis direction is set in advance. The imaging optical system controller 21 calculates the movement amount of the imaging optical system 14 in the optical axis direction on the basis of the input information on the Z-directional position of the cultivation container 50, and outputs a control signal based on the movement amount to the imaging optical system driving section 15. The imaging optical system driving section 15 performs driving on the basis of the input control signal, and thus, the imaging optical system 14 (objective lens 14b) is moved in the optical axis direction, and focus adjustment based on the Z-directional position of the cultivation container 50 is performed.

In this embodiment, since the Z-directional position of the cultivation container 50 is previously detected with respect to each observation region R as described above, a detection timing of the position of the cultivation container 50 with respect to each observation region R and an imaging timing of each phase difference image temporally shift. Accordingly, the movement of the imaging optical system 14 (objective lens 14b) in the Z direction, that is, the auto-focus control is performed after the detection of the position of the cultivation container 50 is performed by the first displacement sensor 18a or the second displacement sensor 18b and before the observation region R reaches the detected position.

Here, in a case where the timing of the auto-focus control is too early, there is a possibility that the Z-directional position of the cultivation container 50 may shift due to some causes after the auto-focus control and before the observation region R reaches the detected position, which may lead to shift in the focus position.

Figure 8:
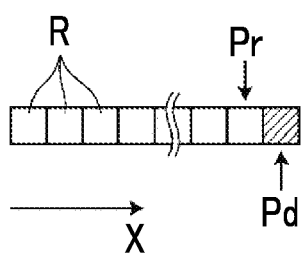
FIG. 8 is a diagram illustrating an example of a timing of an auto-focus control.

Accordingly, it is preferable that the timing of the auto-focus control is a timing immediately before the observation region R reaches the detected position and a timing when capturing of a phase difference image at the detected position is performed enough. Here, it is preferable that the tuning immediately before the observation region R reaches the detected position is a time, for example, as shown in FIG. 8, in a case where the observation region R is sequentially moved in the X direction and the position detected by the detection section 18 is a position pd indicated by oblique lines, from a time point when the observation region R passes a position Pr of the observation region R contiguous to the detected position Pd to a time point when the observation region R reaches the detected position Pd. The auto-focus control may be performed at the time point when the observation region R reaches the detected position Pd.

In this embodiment, a time from a detection timing in the first or second displacement sensor 18a or 18b to a timing of an auto-focus control using position information on a corresponding detected position is set in advance so that the timing of the auto-focus control becomes the above-described preferable timing.

For example, in a case where a moving velocity of the stage 51 is changed by a change of magnification of the phase difference lens 14a, or the like, for example, the preset time may be changed in accordance with the change of the moving velocity of the stage 51. Alternatively, instead of changing the time, in a case where the moving velocity of the stage 51 is changed, a distance between the first displacement sensor 18a or the second displacement sensor 18b and the imaging optical system 14 may be changed by moving the first displacement sensor 18a or the second displacement sensor 18b in the X direction.

Further, as in this embodiment, in a case where the first displacement sensor 18a and the second displacement sensor 18b are provided in parallel. In the X direction with the imaging optical system 14 being interposed therebetween and the position of the cultivation container 50 is detected prior to capturing of a phase difference image, in order to detect the position of the cultivation container 50 and capture the phase difference image in an entire region of the range of the cultivation container 50, as shown in FIG. 5, it is necessary to relatively move the imaging optical system 14, the first displacement sensor 18a and the second displacement sensor 18b up to outside ranges R1 and R2 with reference to the range of the cultivation container 50 in the X direction. Further, it is necessary to secure at least an interval in the X direction between the first displacement sensor 18a and the imaging optical system 14 as the width of the range R1 in the X direction, and to secure at least an interval in the X direction between the second displacement sensor 18b and the imaging optical system 14 as the width of the range R2 in the X direction. In addition, in order to reduce a scanning time of the observation region R as much as possible, it is preferable to narrow a scanning range of the observation region R as much as possible. Accordingly, it is preferable that the width of the range R1 in the X direction is set to the interval between the first displacement sensor 18a and the imaging optical system 14 in the X direction, and it is preferable that the width of the range R2 in the X direction is set to the interval between the second displacement sensor 18b and the imaging optical system 14 in the X direction.

On the other hand, in a case where the observation region R is scanned in the range of the cultivation container 50 by moving the stage 51 in the X direction, it is preferable that the moving velocity of the observation region R in the range of the cultivation container 50 is uniform. Accordingly, at a time when the movement of the stage 51 in the X direction starts, it is necessary to accelerate the stage 51 to reach a uniform velocity, and at a time when the movement of the stage 51 in the X direction ends, it is necessary to decelerate the stage 51 from the uniform velocity for stopping.

Further, in a case where the moving velocity of the stage 51 in the X direction is to be the uniform velocity, it is possible to rapidly control the moving velocity to the uniform velocity without nearly giving an acceleration region, but in a case where such a control is performed, a liquid level of a culture medium or the like contained in the cultivation container 50 together with cells shakes, which may cause lowering in image quality of a phase difference image. In addition, in a case where the stage 51 is stopped, the same problem may occur.

Accordingly, in this embodiment, the range R1 and the range R2 shown in FIG. 5 are set to acceleration-deceleration regions of the movement of the stage 51 in the X direction. By setting the acceleration-deceleration regions on both sides of the range of the cultivation container 50 in the X direction in this way, it is possible to scan the observation region R at a uniform velocity in the range of the cultivation container 50, without uselessly enlarging a scanning range. Further, it is possible to prevent the above-mentioned shake of the liquid level of the culture medium.

Next, returning to FIG. 4, the display controller 23 combines phase difference images of the respective observation regions R imaged by the microscope device 10 to generate one synthetic phase difference image, and displays the synthetic phase difference image on the display device 30.

The display device 30 displays the synthetic phase difference image generated by the display controller 23 as described above. For example, the display device 30 includes a liquid crystal display, or the like. Further, the display device 30 may be formed by a touch panel, and may also be used as the input device 40.

The input device 40 includes a mouse, a keyboard, or the like, and receives various setting inputs from a user. The input device 40 according to this embodiment receives a setting input such as a change command of the magnification of the phase difference lens 14a or a change command of the moving velocity of the stage, for example.

Figure 9:
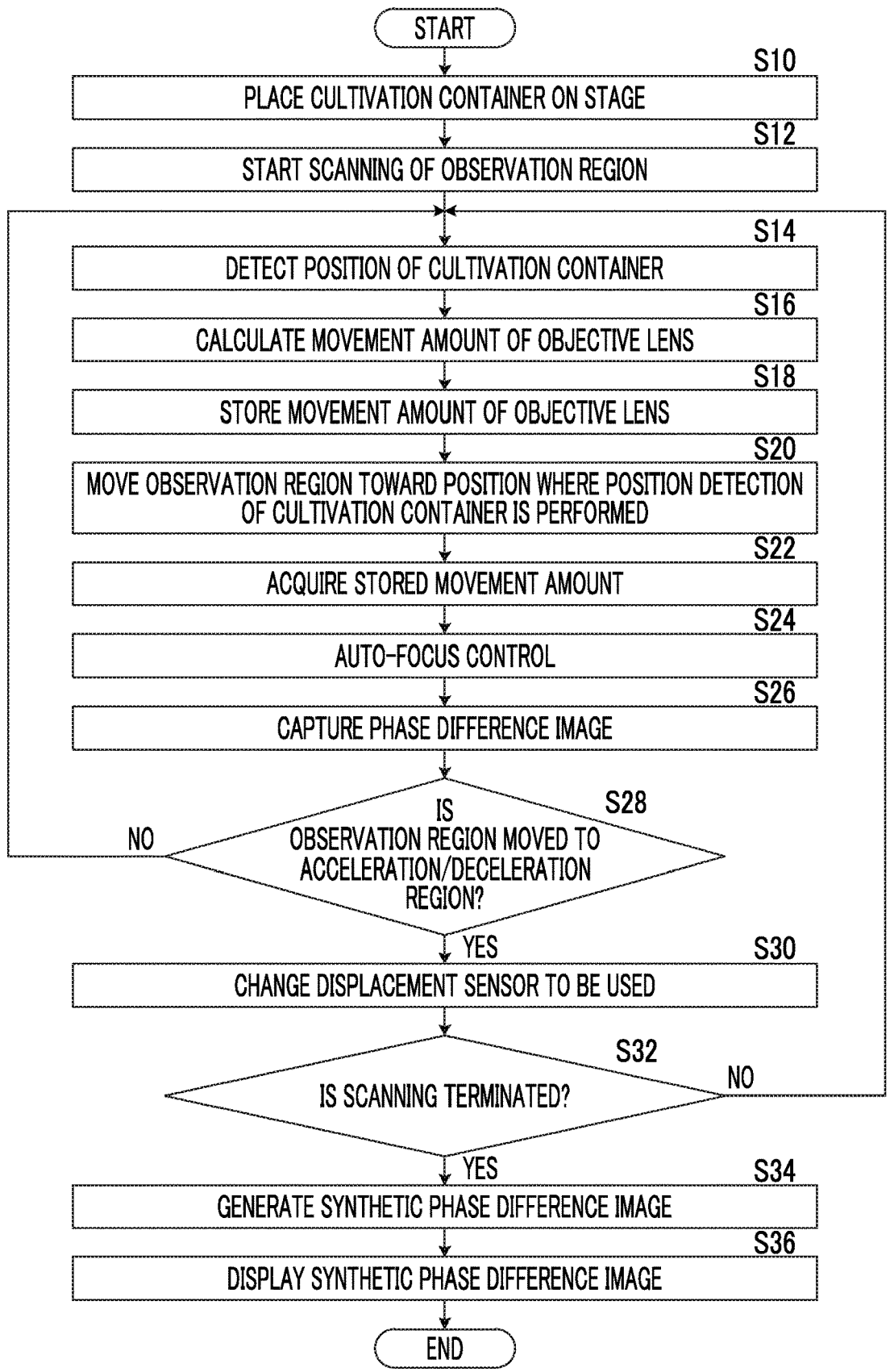
FIG. 9 is a flowchart illustrating an operation of the microscope observation system that uses the observation device according to the first embodiment of the invention.

Next, an operation of the microscope observation system according to this embodiment will be described with reference to a flowchart shown in FIG. 9.

First, the cultivation container 50 in which cells that are observation targets are contained is provided on the stage 51 (S10).

Then, the stage 51 is moved so that the observation region R of the imaging optical system 14 is set at the position of the scanning start point S shown in FIG. 5, and scanning of the observation region R is started (S12).

Here, in this embodiment, as described above, position detection of the cultivation container 50 is precedently performed with respect to each observation region R, and at a time point when the observation region R reaches the detected position, imaging of a phase difference image is performed. The position detection of the cultivation container 50 and the capturing of the phase difference image are performed while scanning the observation region R, and capturing of a phase difference image in the observation region R at a certain position and position detection of the cultivation container 50 at a forward position in a scanning direction with reference to the position are performed in parallel.

Specifically, in a case where the observation region R is moved in the arrow direction in FIG. 6, the Z-directional position of the cultivation container 50 is detected by the first displacement sensor 18a (S14), and information on the detected position is acquired by the imaging optical system controller 21. The imaging optical system controller 21 calculates a movement amount of the imaging optical system 14 (objective lens 14b) in the Z direction on the basis of the acquired information on the Z-directional position of the cultivation container 50 (S16), and stores the movement amount together with a position on X-Y coordinates of a detected position of the cultivation container 50 (S18).

Then, the observation region R is moved toward the position where the position detection of the cultivation container 50 is performed by the first displacement sensor 18a in S18 (S20). Further, the imaging optical system controller 21 reads out the movement amount immediately before the observation region R reaches the position where the position detection of the cultivation container 50 is performed, and performs an auto-focus control on the basis of the movement amount (S22 and S24). That is, the imaging optical system controller 21 controls driving of the imaging optical system driving section 15 on the basis of a movement amount that is stored in advance, and moves the imaging optical system 14 in the Z direction. Then, after the auto-focus control, at a time point when the observation region R reaches the position where the position detection of the cultivation container 50 is performed, capturing of a phase difference image is performed (S26). The phase difference image of the observation region R is output from the imaging element 16 to the display controller 23 for storage. As described above, while the capturing of the phase difference image of the observation region R is performed in S26, the position detection of the cultivation container 50 is performed in parallel at a forward position in the scanning direction with reference to the observation region R.

Further, in a case where the observation region R is moved to the range R2 of the acceleration-deceleration region shown in FIG. 5, is moved in the Y direction, and then, is scanned in an opposite direction in the X direction (S28, YES), that is, in a case where the movement direction of the observation region R is changed from the arrow direction shown in FIG. 6 to the arrow direction shown in FIG. 7, a displacement sensor to be used is switched from the first displacement sensor 18a to the second displacement sensor 18b (S30).

In addition, in a case where the entire scanning is not terminated (S32, NO), the observation region R is moved in the X direction again, and the position detection of the cultivation container 50 and the capturing of the phase difference image described above are sequentially performed (S14 to S26).

A displacement sensor to be used is changed whenever the observation region R is moved up to the acceleration-deceleration region ranges R1 and R2, and the processes of S14 to S26 are repeatedly performed until the entire scanning is terminated. Further, at a time point when the observation region R reaches the position of the scanning end point E shown in FIG. 5, the entire scanning is terminated (S32, YES).

After the entire scanning is terminated, the display controller 23 combines phase difference images of the respective observation regions R to generate a synthetic phase difference image (S34), and displays the generated synthetic phase difference image on the display device 30 (S36).

Figure 10:
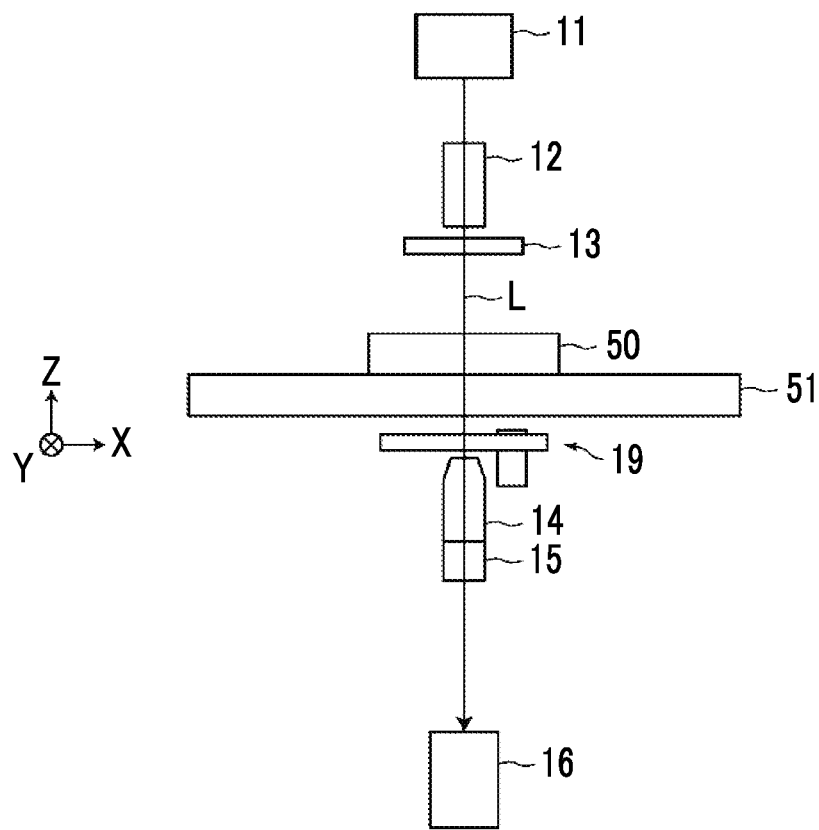
FIG. 10 is a block diagram showing a schematic configuration of a microscope observation system that uses an observation device according to a second embodiment of the invention.

Next, a microscope observation system using a second embodiment of the invention will be described in detail with reference to the accompanying drawings. FIG. 10 is a diagram showing a schematic configuration of the microscope observation system according to the second embodiment of the invention. The microscope observation system of the second embodiment is different from the first microscope observation system of the first embodiment in a configuration of a detection section. Since the microscope observation system of the second embodiment is the same as the first embodiment in the other configurations, hereinafter, the configuration of the detection section of the microscope observation system of the second embodiment will be mainly described.

The detection section 18 of the first embodiment includes two displacement sensors, in which a displacement sensor to be used is changed in accordance with a change of a movement direction of the observation region R. On the other hand, a detection section 19 of the second embodiment includes one displacement sensor, in which a position of the displacement sensor is changed in accordance with a change of a movement direction of the observation region R.

Figure 11:
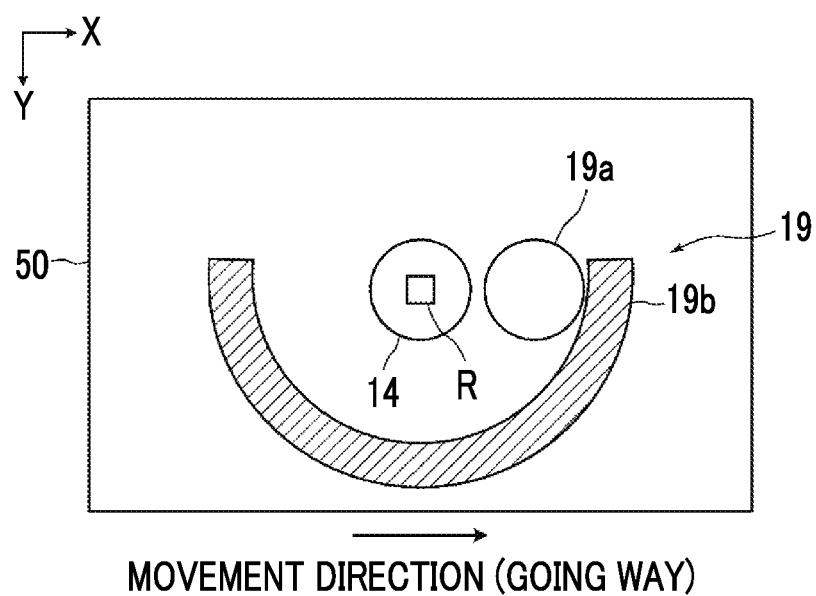
FIG. 11 is a diagram showing a configuration of a detection section of the observation device according to the second embodiment of the invention.
Figure 12:
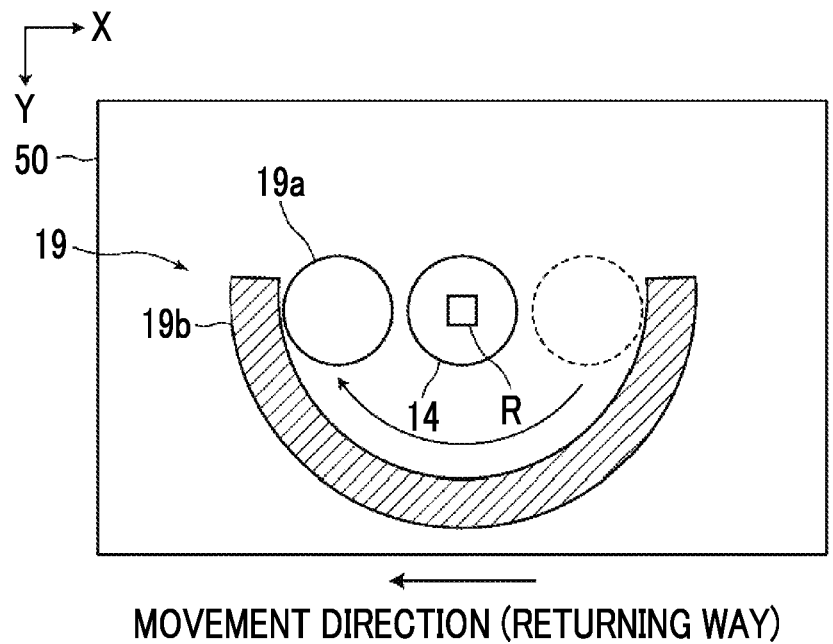
FIG. 12 is a diagram illustrating switching between positions of displacement sensors in the detection section of the observation device according to the second embodiment of the invention.

FIGS. 11 and 12 are diagrams showing a specific configuration of the detection section 19. As shown in FIGS. 11 and 12, the detection section 19 includes a displacement sensor 19a and a guide mechanism 19b that guides the displacement sensor 19a to move its position.

The displacement sensor 19a is the same as the first and second displacement sensors 18a and 18b of the first embodiment. That is, the displacement sensor 19a is configured of a laser displacement sensor.

The guide mechanism 19b includes a semicircular arc-shaped guide member, so that the displacement sensor 19a is moved along the guide member. The guide member moves the displacement sensor 19a from one side to the other side in the X direction with the imaging optical system 14 (objective lens 14b) being interposed therebetween.

FIG. 11 is a diagram showing a position of the displacement sensor 19a in a case where a movement direction of the observation region R is an arrow direction in FIG. 11 (a rightward direction in FIG. 11). On the other hand, FIG. 12 is a diagram showing a position of the displacement sensor 19a in a case where the movement direction of the observation region R is an arrow direction in FIG. 12 (a leftward in FIG. 12). In a case where the movement direction of the observation region R is changed to the arrow direction in FIG. 12 from the arrow direction in FIG. 11, the displacement sensor 19a is moved from the position shown in FIG. 11 along the guide member of the guide mechanism 19b, and is changed to the position shown in FIG. 12.

In this embodiment, the above-described guide mechanism 19b is provided as a displacement sensor moving mechanism for moving the position of the displacement sensor, but the configuration of the displacement sensor moving mechanism is not limited thereto, and other configurations may be used as long as the position of the displacement sensor is capable of being similarly changed.

The other configurations and operations of the microscope observation system of the second embodiment are the same as in the microscope observation system of the first embodiment.

Next, modification examples of the microscope observation systems of the above-described first and second embodiments will be described. In the microscope observation systems of the first and second embodiments, a configuration in which the Z-directional position of the cultivation containers 50 is detected by the detection section 18 or 19 and an auto-focus control is performed using information on the detected position is used, but for example, in a case where a bottom surface of the cultivation container 50 is floated from a mounting surface of the stage 51, or in a case where a bottom portion of the cultivation container 50 is thick, a distance between the imaging optical system 14 and the bottom surface of the cultivation container 50 becomes longer, and thus, even though the imaging optical system 14 is moved in the Z direction to the utmost by the imaging optical system driving section 15, there is a case where the position of the bottom surface of the cultivation container 50 is not included in the range of the depth of field of the imaging optical system 14.

Thus, it is preferable to perform calibration in advance so that the position of the bottom surface of the cultivation container 50 is necessarily included in the range of the depth of field of the imaging optical system 14 by the above-described auto-focus control.

Specifically, for example, in the microscope observation system of the first embodiment, it is preferable to provide a vertically moving mechanism 60 that integrally moves the imaging optical system 14, the imaging optical system driving section 15, the first displacement sensor 18a and the second displacement sensor 18b in the Z direction.

The vertically moving mechanism 60 includes a holding section 60a that integrally holds the imaging optical system 14, the imaging optical system driving section 15, the first displacement sensor 18a, and the second displacement sensor 18b, and an Z-directional driving section 60b that moves the holding section 60a in the Z direction.

The holding section 60a holds the imaging optical system 14, the imaging optical system driving section 15, the first displacement sensor 18a, and the second displacement sensor 18b in a state where relative positional relationships between the imaging optical system 14, the imaging optical system driving section 15, the first displacement sensor 18a, and the second displacement sensor 18b are maintained as they are. The Z-directional driving section 60b includes an actuator such as a piezoelectric element, for example. The vertically moving mechanism 60 is configured to pass a phase difference image formed by the imaging optical system 14 as it is.

Further, before the above-described capturing of the phase difference image is performed, by integrally moving the imaging optical system 14, the imaging optical system driving section 15, the first displacement sensor 18a, and the second displacement sensor 18b in the Z direction using the vertically moving mechanism 60, calibration of an auto-focus control is performed.

Specifically, in the calibration, first, the imaging optical system driving section 15 performs driving to set a Z-directional position of the imaging optical system 14 to a reference position. The reference position refers to a basic position for the above-described auto-focus control, which is a central position of a movement range of the imaging optical system 14 in the Z direction.

Then, an image formed by the imaging optical system 14 is detected by the imaging element 16 at each position while moving the holding section 60a in the Z direction by the Z-directional driving section 60b, and a phase difference image at each position is acquired. Further, a position where contrast of the phase difference image becomes maximum is detected. With respect to the position where the contrast of the phase difference image becomes maximum, for example, a position at which a phase difference image is not focused in a case where the holding section 60a is sequentially moved upward in the vertical direction and a position where a phase difference image is not focused in a case where the holding section 60a is sequentially moved downward in the vertical direction may be detected, and a central position between the detected positions may be detected as the position where the contrast of the phase difference images becomes maximum.

Further, the position where the contrast of the phase difference image becomes maximum is set as the reference position of the vertically moving mechanism 60, and then, the calibration is terminated. The calibration may be performed at a central position of a bottom portion of the cultivation container 50, for example, but may be performed at plural locations of the bottom portion of the cultivation container 50. In this case, an average of reference positions that are respectively detected at the plural locations may be set as a final reference position.

Figure 13:
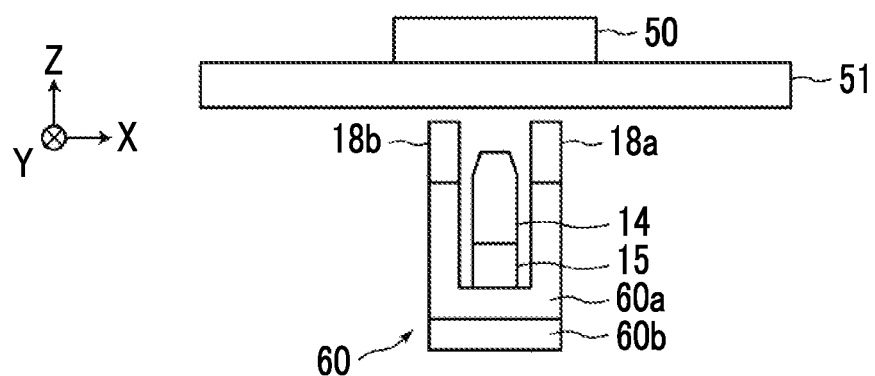
FIG. 13 is a diagram showing an example in which a moving mechanism is provided in a vertical direction with respect to the microscope observation system that uses the observation device according to the first embodiment of the invention.
Figure 14:
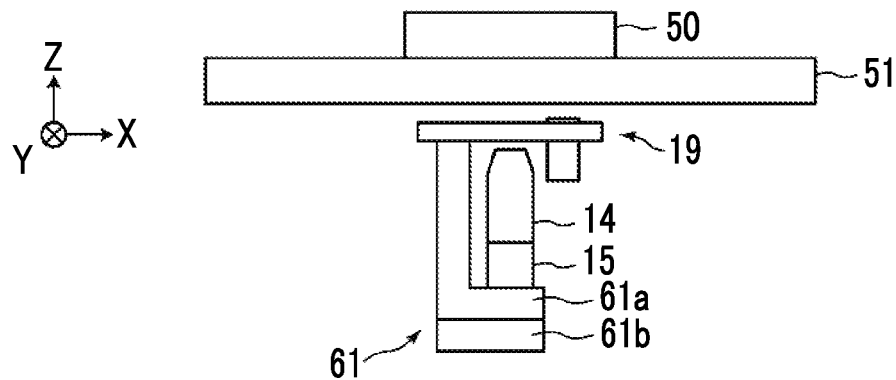
FIG. 14 is a diagram showing an example in which a moving mechanism is provided in a vertical direction with respect to the microscope observation system that uses the observation device according to the second embodiment of the invention.

FIG. 13 is a diagram showing an example in which a vertically moving mechanism 61 is provided in the microscope observation system according to the second embodiment.

The vertically moving mechanism 61 includes a holding section 61a that integrally holds the imaging optical system 14, the imaging optical system driving section 15, and the detection section 19, and a Z-directional driving section 61b that moves the holding section 61a in the Z direction.

The holding section 61a holds the imaging optical system 14, the imaging optical system driving section 15, and the displacement sensor 19a of the detection section 19 in a state where relative positional relationships between the imaging optical system 14, the imaging optical system driving section 15, and the displacement sensor 19a of the detection section 19 are maintained as they are. The Z-directional driving section 61b includes an actuator such as a piezoelectric element, for example, in a similar way to the above-described Z-directional driving section 60b.

A calibration method is the same as in the case of the microscope observation system of the first embodiment.

In the embodiment, a configuration in which the observation region R is scanned by moving the stage 51 is shown, but the invention is not limited thereto. For example, a configuration in which the stage 51 is fixed and the observation region R is scanned by moving the imaging optical system 14 and a different configuration relating to capturing of a phase difference image may be used. A configuration in which the observation region R is scanned by moving all of the stage 51 and the imaging optical system 14 and the configuration relating to the capturing of the different phase difference image may be used.

Further, in the above-described embodiments, the invention is applied to a phase difference microscope, but the invention is not limited to the phase difference microscope, and may be applied to a different microscope such as a differential interference microscope or a bright field microscope.

In addition, in the above-described embodiments, a configuration in which a phase difference image formed by the imaging optical system 14 is captured by the imaging element 16 is shown, but a configuration in which an imaging element is not provided and an observation optical system or the like is provided so that a user is able to directly observe a phase difference image of an observation target formed by the imaging optical system 14 may be used.

EXPLANATION OF REFERENCES

10: microscope device
11: white light source
12: condenser lens
13: slit plate
14: imaging optical system
14a: phase difference lens
14b: objective lens
14c: phase plate
14d: imaging lens
15: imaging optical system driving section
16: imaging element
17: horizontal driving section
18, 19: detection section
18a: first displacement sensor
18b: second displacement sensor
19: detection section
19a: displacement sensor
19b: guide mechanism
20: microscope control device
21: imaging optical system controller
22: scanning controller
23: display controller
30: display device
40: input device
50: cultivation container
51: stage
51a: opening
60, 61: vertically moving mechanism
60a, 61a: holding section
60b, 61b: Z-directional driving section
S: scanning start point
E: scanning end point
L: illumination light
M: observation region scanning position
Pd: detected position
Pr: position of observation region R contiguous to detected position Pd
R: observation region
R1, R2: acceleration-deceleration range
W: well

What is claimed is:

1. An observation device comprising:
a stage on which a container in which an observation target is contained is provided;
an imaging optical system that includes an objective lens for forming an image of the observation target in the container;
an imaging optical system driving section that moves the objective lens in an optical axis direction;
a detection section that includes at least one displacement sensor that detects a vertical position of the container provided on the stage;
an imaging optical system controller that controls the imaging optical system driving section on the basis of the vertical position of the container detected by the detection section;
a horizontal driving section that moves at least one of the stage or the imaging optical system in a main scanning direction in a horizontal plane and a sub-scanning direction orthogonal to the main scanning direction, and reciprocates the at least one of the stage or the imaging optical system in the main scanning direction; and
a scanning controller that controls the horizontal driving section,
wherein the detection section detects the vertical position of the container at a forward position in a movement direction of an observation region with reference to the position of the observation region of the imaging optical system with respect to the container, and changes a position of the displacement sensor in the main scanning direction or the displacement sensor to be used in accordance with a change of the movement direction in the main scanning direction, wherein the detection section includes a displacement sensor moving mechanism capable of moving the displacement sensor in the main scanning direction between one side and the other side with the objective lens being interposed therebetween, and moves the position of the displacement sensor from the one side to the other side in accordance with the change of the movement direction in the main scanning direction.

2. The observation device according to claim 1, wherein the detection section includes at least two displacement sensors that are provided in parallel in the main scanning direction with the objective lens being interposed therebetween, and changes the displacement sensor to be used in accordance with the change of the movement direction in the main scanning direction.

3. The observation device according to claim 1, wherein the displacement sensor moving mechanism includes a guide mechanism that guides the displacement sensor from the one side to the other side.

4. The observation device according to claim 1, wherein the imaging optical system controller controls the imaging optical system driving section to move the objective lens in the optical axis direction at a time point when a predetermined time elapses after the vertical position of the container is detected by the detection section.

5. The observation device according to claim 2, wherein the imaging optical system controller controls the imaging optical system driving section to move the objective lens in the optical axis direction at a time point when a predetermined time elapses after the vertical position of the container is detected by the detection section.

6. The observation device according to claim 3, wherein the imaging optical system controller controls the imaging optical system driving section to move the objective lens in the optical axis direction at a time point when a predetermined time elapses after the vertical position of the container is detected by the detection section.

7. The observation device according to claim 4, wherein the imaging optical system controller controls the imaging optical system driving section to move the objective lens in the optical axis direction at a time point when the observation region of the imaging optical system reaches the detected position or immediately before the observation region of the imaging optical system reaches the detected position after the vertical position of the container is detected by the detection section.

8. The observation device according to claim 5, wherein the imaging optical system controller controls the imaging optical system driving section to move the objective lens in the optical axis direction at a time point when the observation region of the imaging optical system reaches the detected position or immediately before the observation region of the imaging optical system reaches the detected position after the vertical position of the container is detected by the detection section.

9. The observation device according to claim 6, wherein the imaging optical system controller controls the imaging optical system driving section to move the objective lens in the optical axis direction at a time point when the observation region of the imaging optical system reaches the detected position or immediately before the observation region of the imaging optical system reaches the detected position after the vertical position of the container is detected by the detection section.

10. The observation device according to claim 4, wherein the imaging optical system controller changes, in a case where a moving velocity of at least one of the stage or the imaging optical system is changed by the scanning controller, the predetermined time in accordance with the moving velocities before and after the change.

11. The observation device according to claim 5, wherein the imaging optical system controller changes, in a case where a moving velocity of at least one of the stage or the imaging optical system is changed by the scanning controller, the predetermined time in accordance with the moving velocities before and after the change.

12. The observation device according to claim 1, wherein acceleration-deceleration regions for movement of at least one of the stage or the imaging optical system in the main scanning direction are set on both sides of the main scanning direction in the range of the container, and a width of the acceleration-deceleration regions in the main scanning direction and an interval in the main scanning direction between the imaging optical system and the displacement sensor are equal to each other.

13. The observation device according to claim 1, further comprising:
a vertically moving mechanism that integrally moves the imaging optical system, the imaging optical system driving section, and the displacement sensor in a vertical direction.

14. The observation device according to claim 1, wherein the imaging optical system driving section includes a piezoelectric element, and moves the objective lens in the optical axis direction using the piezoelectric element.

15. The observation device according to claim 1, wherein the displacement sensor is a laser displacement sensor.

16. An observation method for moving at least one of a stage on which a container in which an observation target is contained is provided or an imaging optical system that includes an objective lens for forming an image of the observation target in the container in a main scanning direction and a sub-scanning direction orthogonal to the main scanning direction and reciprocating the at least one of the stage or the imaging optical system in the main scanning direction, the method comprising:
detecting a vertical position of the container at a forward position in a movement direction of an observation region with reference to the position of the observation region of the imaging optical system with respect to the container using at least one displacement sensor;
moving the objective lens in an optical axis direction on the basis of the detected vertical position of the container; and
changing a position of the displacement sensor in the main scanning direction or the displacement sensor to be used in accordance with a change of the movement direction in the main scanning direction.

17. A non-transitory computer readable recording medium storing an observation device control program that causes a computer to execute a procedure for moving at least one of a stage on which a container in which an observation target is contained is provided or an imaging optical system that includes an objective lens for forming an image of the observation target in the container in a main scanning direction and a sub-scanning direction orthogonal to the main scanning direction and reciprocating the at least one of the stage or the imaging optical system in the main scanning direction, the program comprising:
- a step of detecting a vertical position of the container at a forward position in a movement direction of an observation region with reference to the position of the observation region of the imaging optical system with respect to the container using at least one displacement sensor;
- a step of moving the objective lens in an optical axis direction on the basis of the detected vertical position of the container; and
- a step of changing a position of the displacement sensor in the main scanning direction or the displacement sensor to be used in accordance with a change of the movement direction in the main scanning direction.

18. An observation device comprising:
- a stage on which a container in which an observation target is contained is provided;
- an imaging optical system that includes an objective lens for forming an image of the observation target in the container;
- an imaging optical system driving section that moves the objective lens in an optical axis direction;
- a detection section that includes at least one displacement sensor that detects a vertical position of the container provided on the stage;
- an imaging optical system controller that controls the imaging optical system driving section on the basis of the vertical position of the container detected by the detection section;
- a horizontal driving section that moves at least one of the stage or the imaging optical system in a main scanning direction in a horizontal plane and a sub-scanning direction orthogonal to the main scanning direction, and reciprocates the at least one of the stage or the imaging optical system in the main scanning direction; and
- a scanning controller that controls the horizontal driving section,
- wherein the detection section detects the vertical position of the container at a forward position in a movement direction of an observation region with reference to the position of the observation region of the imaging optical system with respect to the container, and changes a position of the displacement sensor in the main scanning direction or the displacement sensor to be used in accordance with a change of the movement direction in the main scanning direction,
- wherein acceleration-deceleration regions for movement of at least one of the stage or the imaging optical system in the main scanning direction are set on both sides of the main scanning direction in the range of the container, and a width of the acceleration-deceleration regions in the main scanning direction and an interval in the main scanning direction between the imaging optical system and the displacement sensor are equal to each other.

19. The observation device according to claim 18, wherein the detection section includes at least two displacement sensors that are provided in parallel in the main scanning direction with the objective lens being interposed therebetween, and changes the displacement sensor to be used in accordance with the change of the movement direction in the main scanning direction.

20. The observation device according to claim 18, wherein the imaging optical system controller controls the imaging optical system driving section to move the objective lens in the optical axis direction at a time point when a predetermined time elapses after the vertical position of the container is detected by the detection section.

21. The observation device according to claim 20, wherein the imaging optical system controller controls the imaging optical system driving section to move the objective lens in the optical axis direction at a time point when the observation region of the imaging optical system reaches the detected position or immediately before the observation region of the imaging optical system reaches the detected position after the vertical position of the container is detected by the detection section.

22. The observation device according to claim 20, wherein the imaging optical system controller changes, in a case where a moving velocity of at least one of the stage or the imaging optical system is changed by the scanning controller, the predetermined time in accordance with the moving velocities before and after the change.

23. The observation device according to claim 18, further comprising:
- a vertically moving mechanism that integrally moves the imaging optical system, the imaging optical system driving section, and the displacement sensor in a vertical direction.

24. The observation device according to claim 18, wherein the imaging optical system driving section includes a piezoelectric element, and moves the objective lens in the optical axis direction using the piezoelectric element.

25. The observation device according to claim 18, wherein the displacement sensor is a laser displacement sensor.

* * * * *